United States Patent [19]

Hrebeniuk

[11] Patent Number: Plant 6,150

[45] Date of Patent: Apr. 12, 1988

[54] POINSETTIA PLANT NAMED DYNASTY (H518)

[76] Inventor: Alexander Hrebeniuk, Rd. #1, Box 118, Sugarun, Pa. 18846

[21] Appl. No.: 848,119

[22] Filed: Apr. 4, 1986

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A poinsettia plant named Dynasty (H518) particularly characterized by the combined characteristics of dark red and numerous bracts which form a tight, symmetrical bloom; medium to dark green leaves; dark red and shiny petioles; relatively large bract size, and excellent keeping qualities.

1 Drawing Sheet

The present invention relates to a new and distinct cultivar of poinsettia plant known by the cultivar name Dynasty (H518), and botanically known as *Euphorbia pulcherrima.*

Dynasty (H518) is a product of a planned breeding program which had the objective of creating new poinsettia cultivars with less heat requirement, better breaking, darker red bract color, better keeping, fade resistance, faster rooting, and dark red stems and petioles. Such traits in combination were not present in previously available commercial cultivars.

Dynasty (H518) was originated from a hybridization made in a controlled breeding program by the inventor at Sugarun, Pa. in 1981. The female parent was HL-1, described in applicant's U.S. Plant Pat. No. 4,434. The male parent of Dynasty (H518) was the commercial cultivar V-14, described in U.S. Plant Pat. No. 4,384. Dynasty (H518) was discovered and selected as one flowering plant within the progeny of the stated parentage by applicant Alexander Hrebeniuk in December of 1982 in a controlled environment in Sugarun, Pa.

The first act of asexual reproduction of Dynasty (H518) was accomplished when vegetative cuttings were taken by applicant from the selected progeny in April of 1983 in a controlled environment in Sugarun, Pa. Horticultural examination of selected units initiated in December of 1983 has demonstrated that the combination of characteristics as herein disclosed for Dynasty (H518) are firmly fixed and are retained through successive generations of asexual reproduction.

Dynasty (H518) has not been observed under all possible environmental conditions. The phenotype may vary significantly with variations in environment such as temperature, light intensity, and day length. The following observations, measurements and comparisons describe plants grown in Sugarun, Pa. and Parkerford, Pa. under greenhouse conditions which approximate those generally used in commercial practice.

The following traits have been repeatedly observed and are determined to be basic characteristics of Dynasty (H518) which in combination distinguish this poinsettia as a new and distinct cultivar:

1. Nine week response under black cloth.
2. Four to five breaks after pinch.
3. May be grown single stem or pinched.
4. Top leaves are very dark greenish-blue in color.
5. Mature leaves are medium to dark green.
6. Petioles are very dark red and shiny.

7. Veins in leaves are silver-red on top and bottom.
8. Stems are greenish-red, with the red color becoming darker and more predominant when the plants are grown at low temperatures.
9. Bracts are a very dark red and very fade resistant both in the greenhouse and the home.
10. The centers of the bloom are very tight; cyathia stay on up to four weeks.
11. Red bracts continue to develop even after the cyathia have dropped.
12. Bloom when fresh (ready for shipping) is double and has three rows of bracts.
13. Up to twenty-three (23) bracts have been counted on a fully developed bloom.
14. The largest bloom size measured on a single stem plant has been 18 inches in diameter.
15. Bracts range in size from 3 cm. wide and 4 cm. long to 12 cm. wide and 18.5 cm. long.
16. In normal blooming, the new cultivar shows color by November 15th and the bracts are fully developed by December 10th.
17. Responds well to the growth regulator Cycocel.
18. Plants ship well and will keep up to ten weeks in the home.

The accompanying photographic drawing shows typical inflorescence and foliage characteristics of Dynasty (H518), with colors being as nearly true as possible with illustrations of this type. The single sheet of drawing comprises a black and white photograph with three bracts and a single leaf being in color to accurately depict true color.

In the following description color references are made to The Royal Horticultural Society Colour Chart. The color values were determined at approximately 12:00 noon on Feb. 5, 1986 under natural day light at Sugarun, Pa.

Classification:

*Botanical.*—*Euphorbia pulcherrima.*

*Commercial.*—Poinsettia.

Parentage:

*Male parent.*—V-14.

*Female parent.*—HL-1.

Plant description:

(A) *Form.*—Double.

(B) *Growth habit.*—Upright and compact; taller than V-14, shorter than Eckespoint (Registered Trademark) C-1.

(C) *Rooting.*—Very fast with few problems.

(D) *Blooming season.*—November 15th–December 10th.

(E) *Blooming habit.*—Large bracts in treble rows.

Foliage:

(A) *Size.*—4–5 cm. wide and 7 cm. long to 10 cm. wide and 14 cm. long.

(B) *Quantity.*—Up to ten (10) leaves per stem depending on culture.

(C) *Color.*—New foliage: Upper side, 139A; under side 139B. Old foliage: Upper side, 139A; under side 139B. Leaf petiole: 53A.

(D) *Shape.*—Shape varies from oval to generally heart-shaped to heavily lobed and generally oak shaped; in all forms, tip is acuminate.

(E) *Texture.*—Upper side, velvety between veins; under side, rough because of veins.

(F) *Edge of margin.*—Wavy.

(G) *Aspect.*—Varies from nearly horizontal to upwardly and downwardly inclined.

(H) *Veins.*—Midrib to margin.

(I) *Disease resistance.*—Very resistant to Botrytis.

Flowers (Cyathia):

(A) *Borne.*—Single, very compact inflorescence.

(B) *Quantity.*—No more than ten; each one has a nectary.

(C) *Color.*—Varies widely depending on stage of development; generally orange to orange-red when mature.

Bracts:

(A) *Size.*—3 cm. wide and 4 cm. long when immature up to 12 cm. wide and 18.5 cm. long when fully grown.

(B) *Veins.*—Midrib to margin.

(C) *Quantity.*—Numerous, producing a tight, symmetrical bloom; up to 23 bracts have been counted on a fully developed bloom; bracts continue to develop after cyathia have dropped.

(D) *Color.*—Top: 53B. Bottom: 53C.

(E) *Resistance to fade.*—Excellent, keeping up to ten (10) weeks in the home.

Reproductive Organs: Typical for poinsettia cultivars.

I claim:

1. A new and distinct cultivar of poinsettia plant named Dynasty (H518), as illustrated and described, and particularly characterized by its dark red and numerous bracts which form a tight, symmetrical bloom; medium to dark green leaves; dark red and shiny petioles; relatively large bract size, and by its excellent keeping qualities.

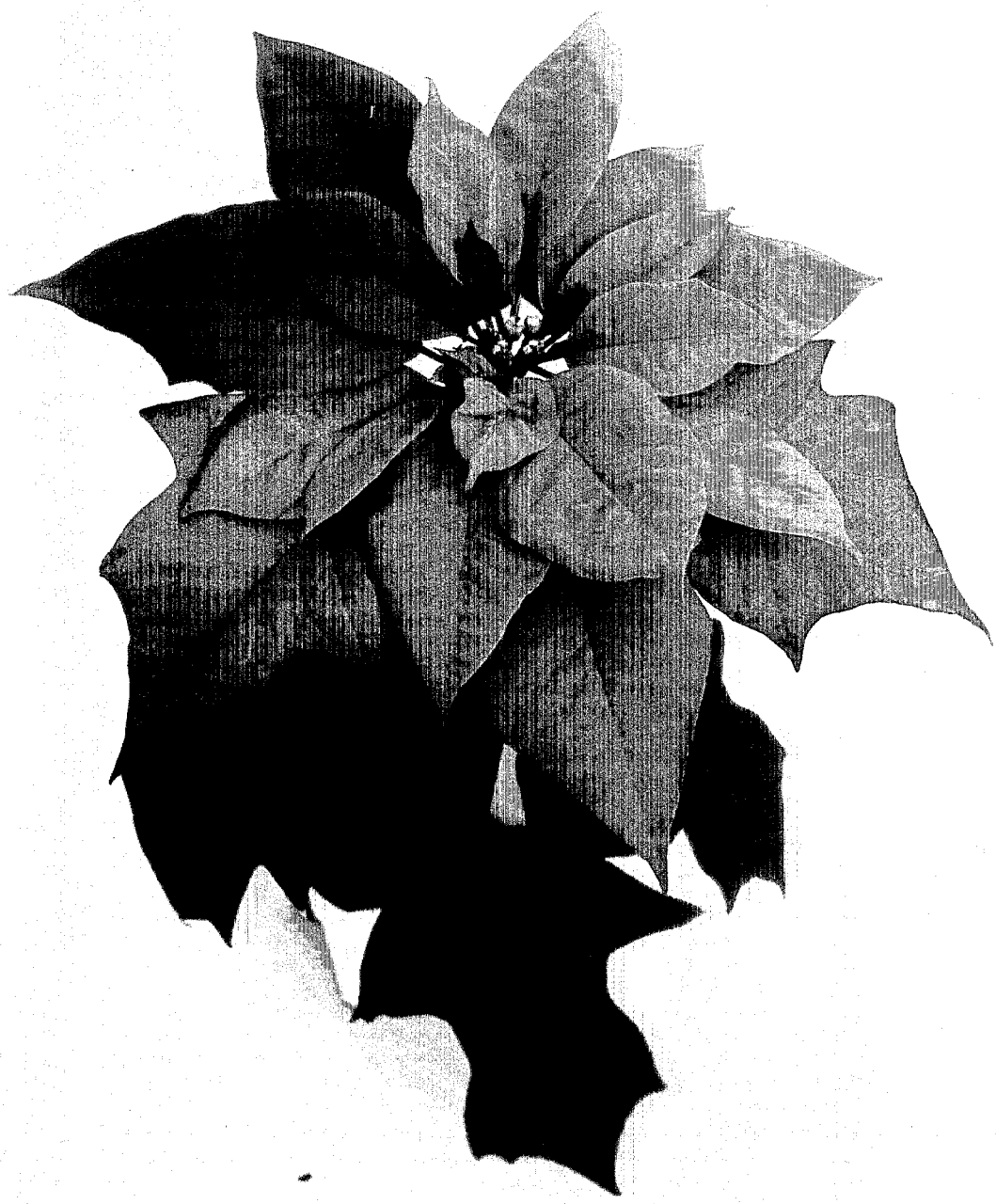

* * * * *